(12) United States Patent
Parrish (10) Patent No.: US 10,080,521 B2
(45) Date of Patent: Sep. 25, 2018

(54) SLEEP APNEA BI-LEVEL POSITIVE AIRWAY PRESSURE MACHINE WITH ADVANCED DIAGNOSTICS AND SELF-CLEANING CAPABILITIES

(71) Applicant: Timothy Joshua Parrish, Templeton, CA (US)

(72) Inventor: Timothy Joshua Parrish, Templeton, CA (US)

( * ) Notice: Subject to any disclaimer, the term of this patent is extended or adjusted under 35 U.S.C. 154(b) by 173 days.

(21) Appl. No.: 15/225,797

(22) Filed: Aug. 1, 2016

(65) Prior Publication Data

US 2018/0028770 A1    Feb. 1, 2018

(51) Int. Cl.
| | |
|---|---|
| *A61B 5/00* | (2006.01) |
| *A61M 16/10* | (2006.01) |
| *A61M 16/06* | (2006.01) |
| *A61B 5/021* | (2006.01) |
| *A61B 5/024* | (2006.01) |
| *A61M 16/08* | (2006.01) |
| *A61B 5/08* | (2006.01) |

(Continued)

(52) U.S. Cl.
CPC .......... *A61B 5/4806* (2013.01); *A61B 5/0002* (2013.01); *A61B 5/021* (2013.01); *A61B 5/02438* (2013.01); *A61B 5/082* (2013.01); *A61B 5/0836* (2013.01); *A61B 5/14542* (2013.01); *A61B 5/6824* (2013.01); *A61B 5/746* (2013.01); *A61M 16/06* (2013.01); *A61M 16/085* (2014.02); *A61M 16/101* (2014.02); *A61M 16/105* (2013.01); *A61M 16/1055* (2013.01); *A61M 16/1075* (2013.01); *A61M 16/0683* (2013.01); *A61M 2016/1025* (2013.01); *A61M 2205/15* (2013.01); *A61M 2205/3334* (2013.01); *A61M 2205/3569* (2013.01); *A61M 2205/3592* (2013.01); *A61M 2205/50* (2013.01); *A61M 2205/502* (2013.01); *A61M 2205/8206* (2013.01); *A61M 2209/10* (2013.01); *A61M 2230/06* (2013.01); *A61M 2230/205* (2013.01); *A61M 2230/30* (2013.01); *A61M 2230/432* (2013.01)

(58) Field of Classification Search
CPC ................ A61M 16/085; A61M 16/10; A61M 16/1005; A61M 16/06; A61M 16/0051; A61M 16/021; A61M 16/022; A61M 16/024; A61M 16/026
See application file for complete search history.

(56) References Cited

U.S. PATENT DOCUMENTS

| | | |
|---|---|---|
| 3,221,733 A | 12/1965 | Beasley |
| 4,197,843 A | 11/1980 | Bird |

(Continued)

*Primary Examiner* — Kristen Matter
(74) *Attorney, Agent, or Firm* — Donald S. Debelak (57) ABSTRACT

A new Continuous/Bi-Level Positive Airway Pressure device (C/BiPAP) that provides positive pressure when the user breathes in and creates negative pressure as the user breathes out. A control system monitors and adjusts oxygen and carbon dioxide levels, and air flow. The device includes the ability to self-clean the mask when it is placed into the housing, the inclusion of a lithium battery for back-up and for use outdoors, and wireless capabilities in the control device. The self-cleaning regime includes a water storage compartment, a water heater, and a tube for steam and warm air running from the water reservoir compartment to the self-cleaning compartment.

9 Claims, 9 Drawing Sheets

(51) Int. Cl.
*A61B 5/145* (2006.01)
*A61B 5/083* (2006.01)

(56) References Cited

U.S. PATENT DOCUMENTS

| | | |
|---|---|---|
| 5,065,756 A | 11/1991 | Rapoport |
| 5,239,995 A | 8/1993 | Estes |
| 5,320,093 A | 6/1994 | Raemer |
| 5,423,313 A | 6/1995 | Olsson |
| 5,743,253 A | 4/1998 | Olsson |
| 6,105,575 A | 8/2000 | Estes |
| 6,349,724 B1 | 2/2002 | Burton |
| 6,367,474 B1 | 4/2002 | Berthon Jones |
| 6,512,938 B2 | 1/2003 | Claure |
| 6,532,960 B1 | 3/2003 | Yurko |
| 6,561,187 B2 | 5/2003 | Schmidt |
| 6,679,257 B1 | 6/2004 | Robertson |
| 7,556,038 B2 | 7/2009 | Kirby |
| 8,136,525 B2 | 3/2012 | Lubke |
| 9,138,169 B2 | 9/2015 | Beard |
| 9,615,773 B1 * | 4/2017 | Kayyali .................. A61B 5/08 |
| 2005/0016536 A1 | 1/2005 | Rapoport |
| 2005/0166922 A1 | 8/2005 | Knepper |
| 2007/0283958 A1 | 12/2007 | Naghavi |
| 2010/0078026 A1 * | 4/2010 | Andrieux .......... A61M 16/024 |
| | | 128/204.21 |
| 2010/0229867 A1 * | 9/2010 | Bertinetti .......... A61M 16/0051 |
| | | 128/205.25 |
| 2017/0000968 A1 * | 1/2017 | Harrington ........ A61M 16/026 |
| 2017/0326322 A1 * | 11/2017 | Lang ................ A61M 16/0875 |

* cited by examiner

SLEEP APNEA BI-LEVEL POSITIVE AIRWAY PRESSURE MACHINE WITH ADVANCED DIAGNOSTICS AND SELF-CLEANING CAPABILITIES

This patent claims the benefit of Provisional Patent 62/088,657, filed on 2014 Dec. 7

PRIOR ART PATENTS

| Patent number | Kind Code | Issue Date | Patentee |
| --- | --- | --- | --- |
| U.S. Pat. No. 3,221,733 | A | Dec. 7, 1965 | Noel F. Beasley |
| U.S. Pat. No. 4,197,843 | A | Apr. 15, 1980 | Forest M. Bird |
| U.S. Pat. No. 5,065,756 | A | Nov. 19, 1991 | David M. Rapoport |
| U.S. Pat. No. 5,239,995 | A | Aug. 31, 1993 | Mark C. Estes, Janice M. Gatano |
| U.S. Pat. No. 5,320,093 | A | Jun. 14, 1994 | Dan Raemer |
| U.S. Pat. No. 5,423,313 | A | Jun. 13, 1995 | Sven-Gunnar Olsson |
| U.S. Pat. No. 5,743,253 | A | Apr. 28, 1998 | Sven-Gunnar Olsson |
| U.S. Pat. No. 6,105,575 | A | Aug. 22, 2000 | Mark C. Estes, Douglas M. Mechlenburg, John H. Fiore |
| U.S. Pat. No. 6,349,724 | B1 | Feb. 26, 2002 | David Burton |
| U.S. Pat. No. 6,367,474 | B1 | Apr. 9, 2002 | Michael Berthon Jones |
| U.S. Pat. No. 6,512,938 | B2 | Jan. 28, 2003 | Nelson R. Claure |
| U.S. Pat. No. 6,532,960 | B1 | Mar. 18, 2003 | Gregory Yurko |
| U.S. Pat. No. 6,561,187 | B2 | May 5 2013 | Mathew F. Schmidt, John S. Baun, Catherine A. Nordman |
| U.S. Pat. No. 6,679,257 | B1 | Jun. 20, 2004 | Christopher John Robertson |
| U.S. Pat. No. 7,556,038 | B2 | Jul. 7, 2009 | Ted Kirby, Leonardo A. Balboa, Erik K. Witt |
| U.S. Pat. No. 8,136,525 | B2 | Mar. 20, 2012 | Steven John Lubke |
| U.S. Pat. No. 9,138,169 | B2 | Sept. 22, 2015 | John S. Beard |

FIELD OF THE INVENTION

This invention relates to a new Bi-Level Positive Airway Pressure device (BiPAP) that delivers breathing gas such as air, oxygen or a mixture thereof at relatively higher and/or lower pressures than normal breathing from the end user to minimize sleep disorders from partial or complete upper airway obstruction.

BACKGROUND

BiPAP (Bi-Level Positive Air Pressure) devices or Bi-level PAP are breathing devices that use bi-level positive airway pressure to treat patients with central and obstructive apnea.

Bi-level positive airway pressure means that the machine delivers air under higher pressure as the sleeper inhales, and switches to a lower pressure during exhalation to make it easier to breathe out. Some of the benefits of a BiPAP machine include: 1) patients have good respiratory rates with BPAP machines; 2) the therapy is effective in terms of clinical status and improvement in blood gas levels; 3) the technology for BiPAP, named expiratory pressure relief (C-Flex), monitors the patient's airflow during his/her expiration and the air pressure is adjusted in response to the patient's needs. Toward the end of the expiration, the pressure is increased again to prevent airway collapse.

The core of a Bi-Flex Pressure Relief system is an adaptive flex pressure relief system called Bi-Flex to sense your breathing patterns and then provide pressure relief at key points during inhalation and exhalation to provide a more natural breathing experience. The air pump is within the housing with simple processor controls and readouts connected to a mask that fits over the nose and mouth, with the air hose running into the mouth.

The current state of commercial products is that BiPAP machines are a breathing apparatus that optimizes the positive pressure to the airway of a patient. The apparatus is configured to detect flow limitations in the patient airway from an analysis of inspiratory flow waveforms. The airway pressure settings is raised, lowered or maintained depending on whether a flow limitation has been detected.

The standard BiPAP product does not include readings of oxygen sensor levels, CO2 levels, and blood pressure. These are important readings especially since some users of BiPAP machines also use oxygen during the night. BiPAP machines do not commonly include a supply of oxygen, nor do they have a blood pressure monitor. While the standard BiPAP machine has a sensor to determine when the user is breathing in and breathing out, it doesn't provide additional diagnostics, including monitoring when the patient is in distress, resting energy levels, and respiration levels.

There are separate pieces of equipment to these tasks, oxygen masks, see patent #U.S. Pat. No. 9,138,169 B2, infrared sensors are used in pulse oximeter which is placed on the finger, see U.S. Pat. No. 5,995,859A, and wrist based blood pressure monitors, but no product currently on the market or currently with a patent or patent application includes all these features in one unit with a processor cable of reading the data and reacting to the data.

Other potential useful features that current products don't include are self-cleaning features for the mask. This is a major drawback for users as bacteria can form in the mask. Another drawback is a lack of battery backup, both for use in the home if power goes out, or if the user goes and in the woods. Current equipment also does have data logging capabilities or the ability to transfer data wirelessly to an outside monitoring site.

The deficiencies as listed above in current equipment include:
1. no readings of O2 levels and no ability to add O2 supply and or to adjust O2 supply as needed;
2. no ability to measure exhaled flow and O2 and CO2 levels;
3. no ability to take blood pressure readings;
4. no self-cleaning capabilities;
5. no battery backup;
6. no ability to measure respiratory levels;
7. no ability to measurement of resting energy levels;

8. the lack of a processor capable of reading CO2, O2 and exhaled air flow;
9. the lack of a processor capable of taking CO2, O2, and in and out airflow measurements and dictating changes in operation as required, setting of alerts when required, data logging readings and information at appropriate intervals and wireless transferring of that data to an outside source.

Some of the current deficiencies have been covered by patents by others. Adding the ability to read and adjusting oxygen levels has been addressed by U.S. Pat. No. 6,512,938 and patent U.S. Pat. No. 6,561,187 and application US 20070283958. The ability to measure respiratory levels, which is an additional and useful feature, is addressed in U.S. Pat. No. 6,532,960. The ability to measure resting energy is addressed in U.S. Pat. No. 6,532,960. The ability to measure the exhaled air for O2 and CO2 levels is addressed in U.S. Pat. No. 7,556,038.

No patent, patent application or current product on the market address the need for battery back-up or self-cleaning. These are the two unique features being added to the BiPapp machine in the proposed device in this application. Nor do patents, patent applications or current products have a process designed to take CO2, and O2 measurements, and in and out airflow measurements dictating changes in operation as required, as well as setting off alerts when required.

DESCRIPTION OF PRIOR ART

U.S. Pat. No. 3,221,733 is a sleep apnea correcting devices that deals with using alternating periods of air pressure, either compressed air or oxygen, with periods of no pressure.

U.S. Pat. No. 4,197,843 is a device that uses a bellow system to control air into a mask or similar device with periods of no pressure to allow the user to exhale.

U.S. Pat. No. 5,065,756 is the first device related to continuous pressure to a nose mask, with vents in the mask to allow the pressure to drop while the user exhales. The mask does not cover the mouth. Key points of this invention are establishing a threshold control value, and the vent holes in the mask to allow user to more efficiently exhale.

U.S. Pat. No. 5,239,995 covers the use of high and low pressure to a sleep apnea device that corresponds to the users respiratory patterns.

U.S. Pat. No. 5,320,093 deals with a method of measuring CO2 gas in a patient after surgery coming out of anesthesia and adjusting the CO2 level as needed.

U.S. Pat. No. 5,423,313 deals with having two lines with two different air streams to a respirator, such as a stream of O2 and compressed air, each stream being regulated. The gas supply also pulses as the air flow. This patent calls for two separate respirators. The patent deals with tracheal tubes as the delivery device rather than a mask, but the use of two air streams still applies.

U.S. Pat. No. 5,743,253 is by the same inventors as U.S. Pat. No. 5,423,313 and covers the measuring of the pressures of the air steams being delivered.

U.S. Pat. No. 6,105,575 involves applying separate and independent adjustments to flow rates of pressurized gas delivered to a patient during inspiratory and expiratory phases of a respiratory cycle U.S. Pat. No. 6,349,724 involves a device that monitors the breathing of a sleep apnea patient and then regulates high and low pressure to correspond to the breathing pattern of the patient.

U.S. Pat. No. 6,367,474 improves over prior art of U.S. Pat. No. 6,349,724 by measuring the breathing of the patient and providing air flow at a higher rate when an apnea event occurs, then lower air flow when apnea is not occurring rather than provide air on a continuing basis.

U.S. Pat. No. 6,512,938 deals with monitoring O2 levels in patients and then adjusting the O2 levels based on those results.

U.S. Pat. No. 6,532,960 is a further improvement on sleep apnea design where the device monitors the user's respiration and then responds with different levels of pressure U.S. Pat. No. 6,532,960 measures a sleep apnea patient resting energy to determine if the pressure should be adjusted.

U.S. Pat. No. 6,561,187 discusses various methods to control oxygen flow through a monitoring process.

U.S. Pat. No. 6,679,257 proposes a mouth piece rather than a nose piece delivery system for the air pressure to a sleep apnea patient.

U.S. Pat. No. 7,556,038 includes monitoring respiration of a user and determining a user breathing frequency including an inspiration portion and an expiration portion of the breathing U.S. Pat. No. 8,136,525 is for a mask device that is more comfortable delivering a breathable gas to the patient, the device includes a mouth cushion, a pair of nasal prongs, an elbow, and a headgear assembly.

U.S. Pat. No. 9,138,169 is for a mask that includes covering both the nose and the mouth for equipment designed for use for sleep apnea sufferers.

SUMMARY OF THE INVENTION

This device incorporates many of the features of currently on the market, plus incorporating some of the additional features that have appeared in patent applications, but adds four new features to field, a self-cleaning chamber; a lithium battery component; data logging capabilities; and Wi-Fi (wireless) capabilities to send data to an outside data collection point. This device in this application is referred to as C/BiPaP for Continues Bi-level Positive Airway Pressure device, as it assists the user during both the inhaling and exhaling breathing cycle. The features of the invention includes the items listed below.

1. A breathing circuit, one end of which includes a patient interface device such as a nasal face mask.
2. A first integrated control unit using ASCII Infrared technology configured to read and adjust flow rates to and from the patient, oxygen levels, carbon dioxide levels (read only) and heart rate (read only).
3. A second integrated control unit able to monitor and report waveforms of air flow to and from the patient.
4. A wrist mounted blood pressure monitor that can send blood pressure and heart rate readings to the microprocessor.
5. A microprocessor configured to;
   h. accept input for limits of acceptable compressed air flow rates, O2 levels, CO2 levels and blood pressure;
   i. calculate respiratory patterns base on flow rates, oxygen levels and heart rate;
   j. detect flow limitations in the patient airway from an analysis of inspiratory flow waveforms;
   k. Determine resting energy of user from inputs;
   l. Initiate alerts when readings for when O2, CO2, blood pressure, air flow, or resting energy levels fall below set limits;

m. Data log data from each sensor, as well as calculations for respiratory patterns, and resting energy levels;

n. Communicate wirelessly to a computer either on or off-site.

6. A mask that with air and oxygen ports that allows the exhaled air through a third port to be sent through CO2 and O2 sensors that use infrared technology located in the mask with the data sent to the integrated control unit.

7. A bi-directional circulating pump that both pushes airflow to the user and pulls exhaled air from the user.

8. A self-cleaning feature that with a procedure that includes activation with a button or toggle. The self-cleaning feature includes a heater to and a water reservoir to heat up and steam the hose and mask.

9. A cone shape housing with the top acting as a storage compartment for the mask. The top storage compartment is also the area in which the mask is cleaned.

10. A lithium battery both for battery back-up and so the device can be used in outdoor activities when required.

Additional embodiments can include a variety of additional features including:

1. adding an oxygen sensor to determine the oxygen saturation level of the patient;
2. adding an oxygen port located on the mask to direct oxygen directly to the user rather than adding oxygen to the air flow from the C/BiPAP device;
3. adding an oxygen concentrator communicatively linked to the oxygen sensor;
4. adding a carbon dioxide meter to determine a metabolic rate of the patient;
5. adding an emergency condition system with audible alerts and alerts transferred wirelessly to a receiving station. The alerts can be activated by an air leak, power failures or irregularities, or a radical change in air flow pressure;
6. adding response capabilities to emergency alerts including-engaging a backup power supply for the C/BiPAP device, opening an emergency valve to provide ambient air to the user;
7. incorporating a humidifier circuit including a heater/cooler, a humidifier, a filter, a communication interface, a monitor and a medication chamber;
8. adding a pulse meter;
9 adding a blood pressure reading device;
10. adding a heart rate monitor;
11. adding a communication device that transmits information between the patient and a medical professional or monitoring system.

DETAILED SUMMARY OF THE INVENTION

The standard features of the invention which are included in the housing.

1. CO2 sensor, an ASCII sensor infrared monitoring sensor that will analyze Bi-level positive airway pressure and read data from a display panel.
2. UV Flux 25% Oxygen Sensor will measure ambient O2 levels in 0-25% in the patient. This sensor will benefit the user by measuring the oxygen pressure and temperature compensation. Both are vital for patients who need to use oxygen along with their Bi-level Positive airway pressure machine.
3. The housing will be a cone shaped on top which will and act as a storage compartment for the mask. This will keep the mask clean from dust particles and other particulates when not used.
4. This device will have a feature to self-clean the mask. The self-cleaning procedure will consist of pushing a button toward the top of the housing which can be pushed to activate the self-cleaning mode. The device will have a heater to and a water reservoir to heat up and steam the hose and mask.
5. The top of housing can be opened for storage of the mask and hose.
6. The continuous Bi-level Positive Airway machine will be shaped like a cylinder—see drawings.
7. The Continuous Bi-level Positive Airway Pressure device will have a built in battery that will back the unit up when there is a power outage. The battery life will be 4-6 hours.
8. The processor will include the control of a CO2 data logger, infrared O2 sensor, and blood pressure monitor, and it can incorporate a variety of sensors including NDIR, electro-chemical and MOS. The air flow from the ports on either side of the mask will have airflow activated by pumps within the module if needed.
9. The process will include alerts when CO2 levels, blood pressure or O2 levels fall out a prescribed range that is entered in to unit
10. The C/BiPAP device will be compatible for both with apple IOS and android IOS systems for sleep mapping and data use.
11. The C/BiPAP device will have a display with an Interactive touch screen display.

The standard features of the invention which are included in the mask of the device.

1. A foam piece(s) or other comfort material for the user to apply underneath the mask for comfort.
2. Additional strapping and size to accommodate the ports that send airflow back to the sensors for reading.
3. A feature that at prescribed times sends air flow from the end user after breathing out is returned to where CO2 and O2 levels can be read and shown on the monitor.
4. Alarms are set off if CO2 and/or O2 levels, or blood pressure, fall out of a prescribed range.
5. A self-cleaning function is activated when the mask is set back into the housing and the top closed.

Standard features of the invention which are included in the blood pressure wrist monitor are: the wrist monitor can communicate with C/BiPAP processor and that the pump in the wrist band has positive pressure on the band.

The Self Adjusting Breathing Cycle Software

The Self Adjusting Breathing Cycle Software works with data from the wrist pulse reader, O2 readings, CO2 readings, air pressure in and air pressure out readings to synchronize breathing during all cycles of operation. The Continuous Bi-level Positive Airway Pressure device (C/BiPAP) will provide a complete diagnostic system to monitor key levels of CO2, O2, and blood pressure in order to sound alerts when problems occur.

Operation of the Display
    Icons on the first menu
On/off Icon
    Icons on second menu
Air flow to Patient
Air flow from Patient
Humidity
Monitoring levels
Use last settings
Time Adjustment
Ramping
Alarm
Heart Rate
Data
Enter

DRAWINGS

Figures

PART NUMBER DESCRIPTIONS

1. Air hose.
2. Air hose holder on the mask cleaning chamber cover.
3. Mask cleaning chamber cover.
4. Opening in mask cleaning chamber cover.
5. Air hose connection during self-cleaning.
6. Mask cleaning chamber.
7. Touch screen digital display.
8. Start button push once on/off push twice for the mask self-cleaning function.
9. Air filter hose connection (which goes to the mask 45).
10. Temperature sensor.
11. Memory/data logger module.
12. Chamber that holds data logger, processor, pumps, and battery.
13. Processor module and alarm.
14. Battery module.
15. Wi-Fi/Bluetooth antenna.
16. Door for removing water reservoir module from water reservoir chamber.
17. Chamber of housing for removable water reservoir.
18. Hinge for opening door for removing water reservoir module.
19. Removable water reservoir.
20. Metal heat conveyance module for warming water,
21. Ceramic heating unit.
22. Ceramic heating unit chamber.
23. Retractable power cord storage chamber.
24. Power cord retraction/winding mechanism.
25. Hinge for mask cleaning chamber lid.
26. Solar cell.
27. Intake valve for oxygen supply.
28. Waste water hose with drain.
29. Two way air intake valve with a pressure release.
30. Bi-directional pump for air and water to send air to the mask.
31. Two-way air valve with a pressure release.
32. One-directional pump to clean air and water from the mask cleaning chamber.
33. Magnetic door closure bar.
34. Waste water reservoir chamber.
35. Door to remove waste water reservoir for waste water receptacle.
36. Hinge for the door to remove the waste water reservoir.
37. Removable waste water reservoir.
38. Retractable power cord.
39. Mask strap.
40. Connection piece from mask to strap.
41. Platform for mask comfort material.
42. Comfort material for mask.
43. CO2 and O2 monitoring device with wireless capability.
44. Mask air hose connector/filter.
45. Mask.
46. Air filter material.
47. Air filter liner.
48. Pulse reader.
49. Digital display on pulse monitoring wristband.
50. Pulse monitoring armband.
51. Armband clasp system.
52. Human (user) head.
53. Mask headband.
54. Mask headband clasp.
55. Mask connection to air hose.
56. Right flexible hose to right nasal bud.
57. Left flexible hose to left nasal bud.
58. Right nasal bud.
59. Left nasal bud.
60. Air flow icon.
61. Humidity icon.
62. Monitoring levels icon.
63. Data logger icon.
64. Use last settings icon.
301. Closed position mask cleaning chamber lid.
302. Half open position mask cleaning chamber lid.
303. Full open position mask cleaning chamber lid.
304. Path of travel mask cleaning chamber lid.

DETAILED DESCRIPTION OF DRAWINGS

Figure 1:
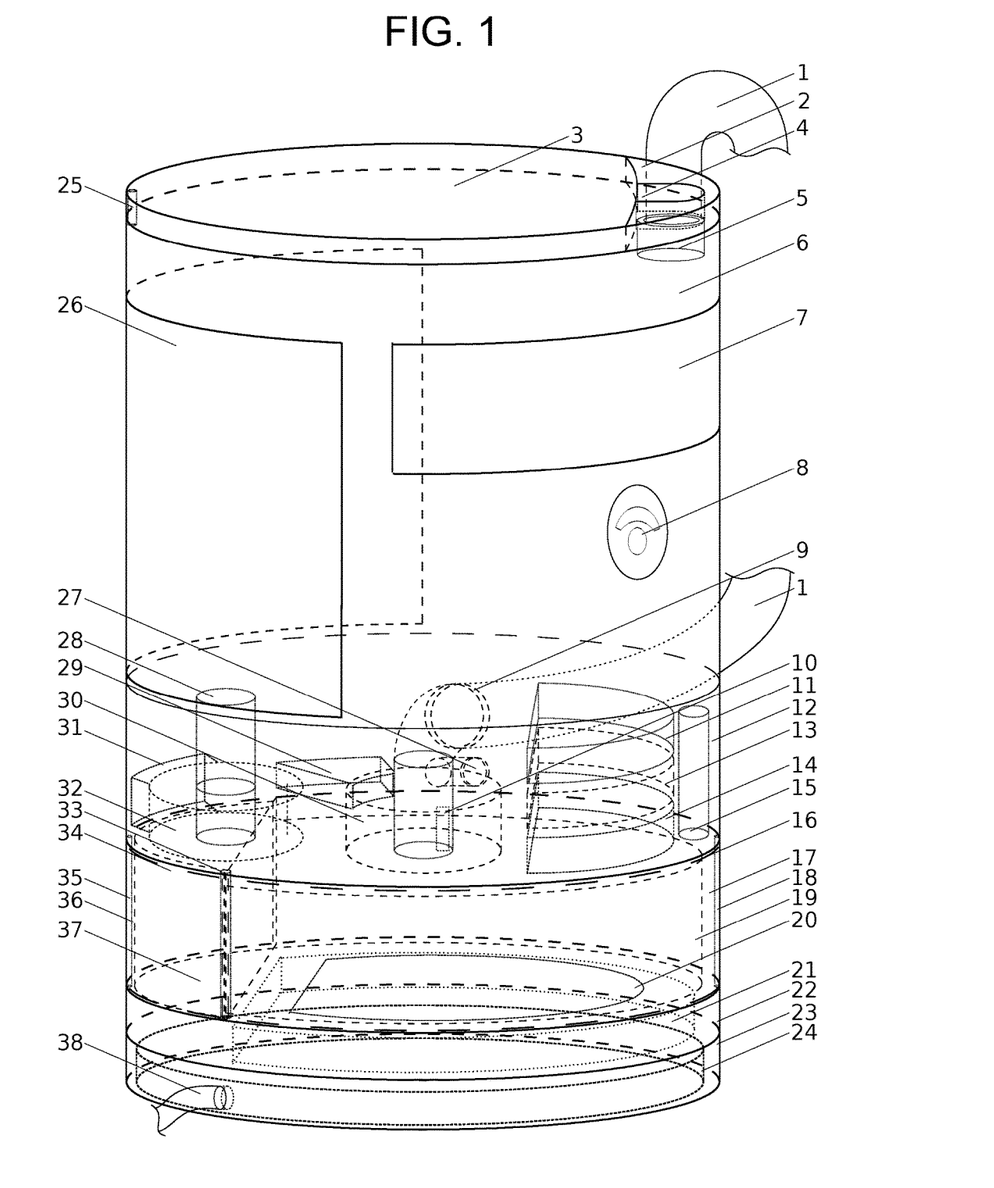
FIG. 1 is an inside and outside look of housing for the device.

FIG. 1 is an inside and outside look of housing for the device. A mask cleaning chamber cover 3 which is opened by the use of a hinge 25. The air hose 1 is included in the cleaning process by inserting the air hose 1, which in normal operation goes to the mask, into the air hose holder 2 on the mask cleaning chamber cover. The air hose holder is positioned in the opening of the mask cleaning chamber cover 4. The cleaning process is initiated by pushing the start button 8 twice for the mask cleaning operation. Note: The start button 8 pushed once turns the device on. If the device is on, pushing the self-leaning device start button 8 once will start the self-cleaning process. If the device is off, the start button 8 must be pushed twice, once to start the device, and once to start the self-cleaning process. The cleaning process is initiated by starting up the ceramic heater unit 21; which is positioned in a ceramic heating element chamber 22, which allows the ceramic heating element to rest against the bottom of the removable water reservoir, which has a bottom portion made of metal impregnated plastic 20. Vents (not shown in the drawing) in the top of the removable water reservoir 19, floor of and top of the chamber that holds data logger, processor, pumps, and battery 12 allows the warm air and steam to rise into the mask cleaning chamber. Once the mask cleaning procedure is complete the one-directional (vacuum) pump 32 is activated to clear the water and air in mask cleaning compartment 6 through the waste water hose with drain 28. If excess pressure from the pump is accumulated in the evacuation process it is released through the air valve with a pressure release 31. Waste water drawn out by the one-directional pump 32 goes into the removable waste water reservoir 37.

When the Continuous Bi-Level Positive Airway Pressure (C/BiPAP) device is started the air hose 1 is disconnected from the air hose holder on the mask cleaning chamber cover 2 and directed to the mask air hose connector/filter 44. Not shown in the drawings is that there is an opening with a gasket in the wall of the mask cleaning compartment 6 and an opening with a gasket from the ceiling of chamber that holds data logger, processor, pumps, and battery 12 to the mask cleaning compartment 6 so that the hose can travel from the bi-directional pump 30 through the air hose filter connection 9 to the mask 45.

Once the mask is secure on the user the bi-directional pump for air and water 30 is activated with the display 7 to send air to the mask 45. The bi-directional air pump brings water vapor from the removable water reservoir 19 and takes in air from the chamber that holds data logger, processor, pumps, and battery 12, which also pulls air through the vents in the floor of the mask cleaning compartment 6 through the two way air intake valve with a pressure release valve 29. The bi-directional pump 30 sends air to the mask 45 for a time preset on the touch screen display 7 for breathing and then for a time preset on the digital display 7, pulls air back from the user (vacuum operation) while the user exhales. If the air pressure is too high it is released through the two way air intake valve with a pressure release 29. In cases where the user requires oxygen, oxygen is delivered to the air filter hose connection to the mask 9 through intake valve for oxygen supply 27. Not shown in the figure is the oxygen line which leaves through a port with a sealing gasket to the outside oxygen supply.

During the exhaling process of the user CO2 and O2 levels are monitored by the CO2 and O2 monitoring device with wireless capability 43 which send information wirelessly to the processor module 13. The processor module 13 has the capability of adjusting air and oxygen supply levels and times sequences for user inhaling and exhaling cycles based on CO2, O2, and pulse reading levels (from the digital display 49 on the pulse monitoring armband 50 which send pulse readings to the processor wirelessly.) The processor module 13 receives the data from the CO2 and O2 monitoring device 43 and the digital display 49 of pulse reading armband 50 through a Wi-Fi/Bluetooth antenna 15. The data received by the processor is stored in the memory/data logger module 11 which can be accessed wirelessly the through the Wi-Fi/Bluetooth antenna 15 by outside computers or computer type devices including pads and smartphones.

The removable water reservoir 19 is removed by opening the door for removing the water reservoir module from water reservoir chamber 16, using the hinge for opening door for removing the water reservoir module 17.

Other items of note on FIG. 1 include a solar powered battery 14, a solar cell 26 for charging the battery (note electrical connections between solar cell and battery are not shown), the retractable power cord 38, the compartment for the retractable power cord 23 and power cord retraction/winding mechanism 24.

Figure 2:
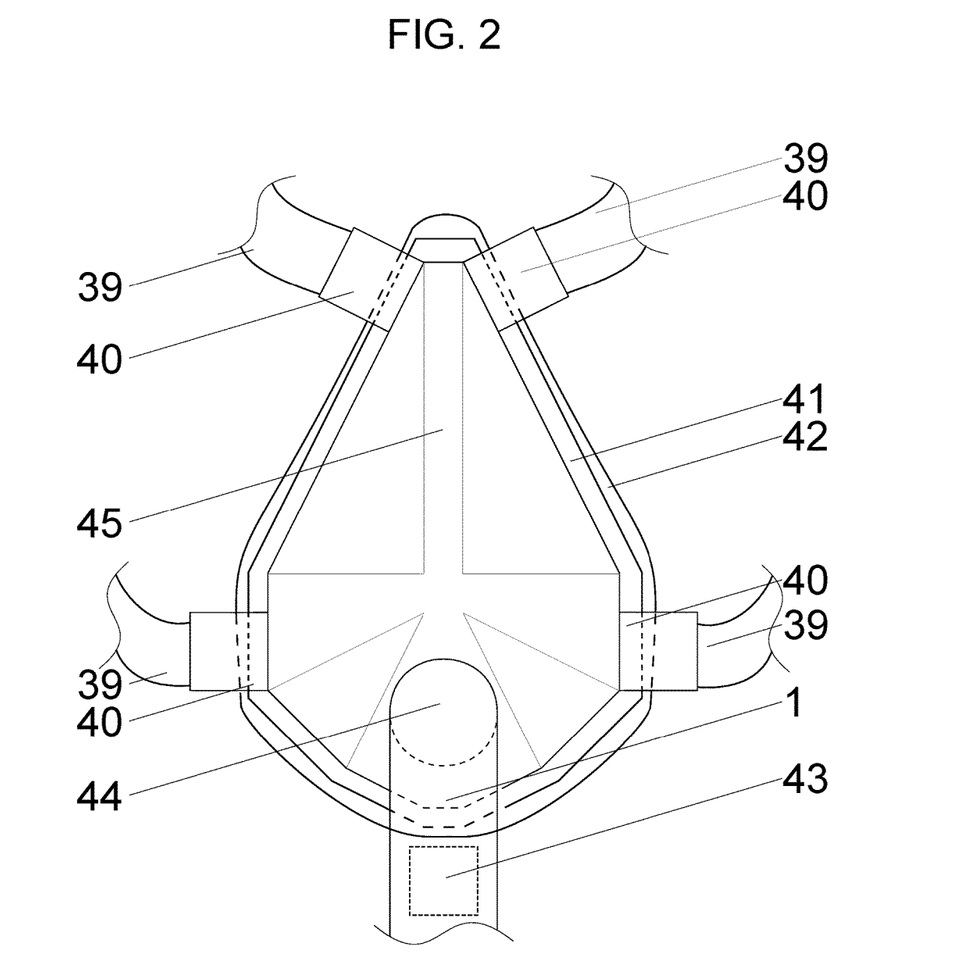
FIG. 2 is the mask that provides positive pressure to the end user and also sends air back to the housing for O2 and CO2 monitoring.

FIG. 2 shows the mask 45 (in an upside down view, with the top on the bottom, and the bottom on top) that provides positive pressure to the end user through the air hose 1 which connects to mask air hose connector/filter 44 and also sends air back to the device when the bi-directional air/water pump 28 is pulling exhaled air away from the user. During the exhale process CO2 and O2 monitoring occurs through the CO2 and O2 monitoring device with wireless capability 43. The mask 45 fits over the patients mouth and nose and has an opening for the hose 1 that bring in air to develop a positive air pressure for the housing. The mask 45 has a platform comfort material platform 41 which holds comfort material 42 for the mask 435. The mask 45 is held around the head with a mask strap 39 and connection pieces from mask to strap 40.

Figure 3:
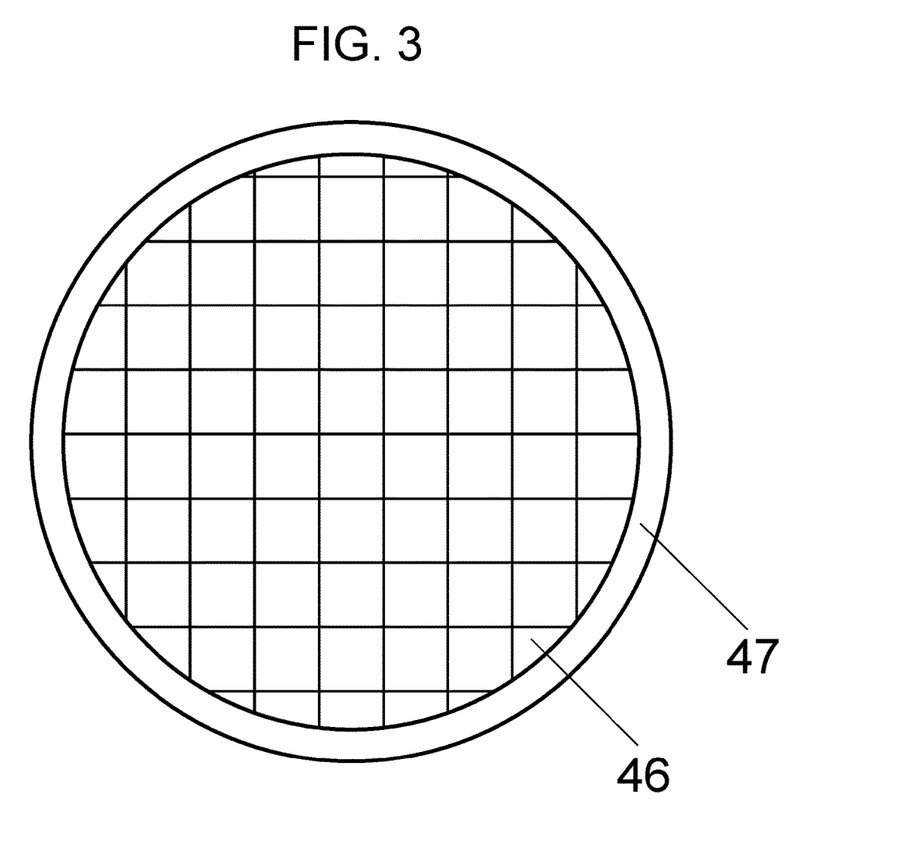
FIG. 3 is a picture of the filter that is between the air input tube and the mask.

FIG. 3 shows the filter in the mask air hose connection/filter 44. The filter has air filter liner 47, and filter material 46.

Figure 4:
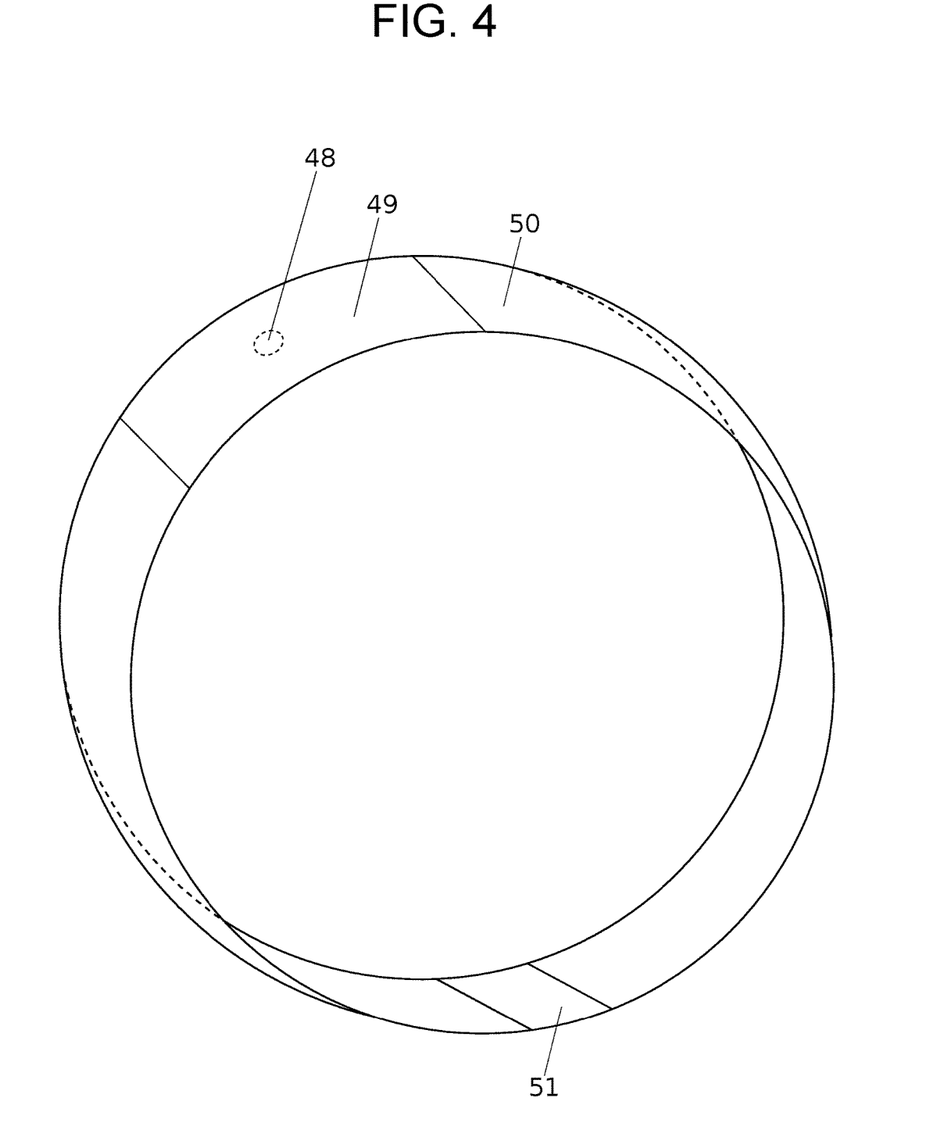
FIG. 4 is armband with display for reading patient's pulse

FIG. 4 show the pulse reading arm ban 50, with its pulse reader 48, digital display 49 and arm band clasp system 51.

Figure 5:
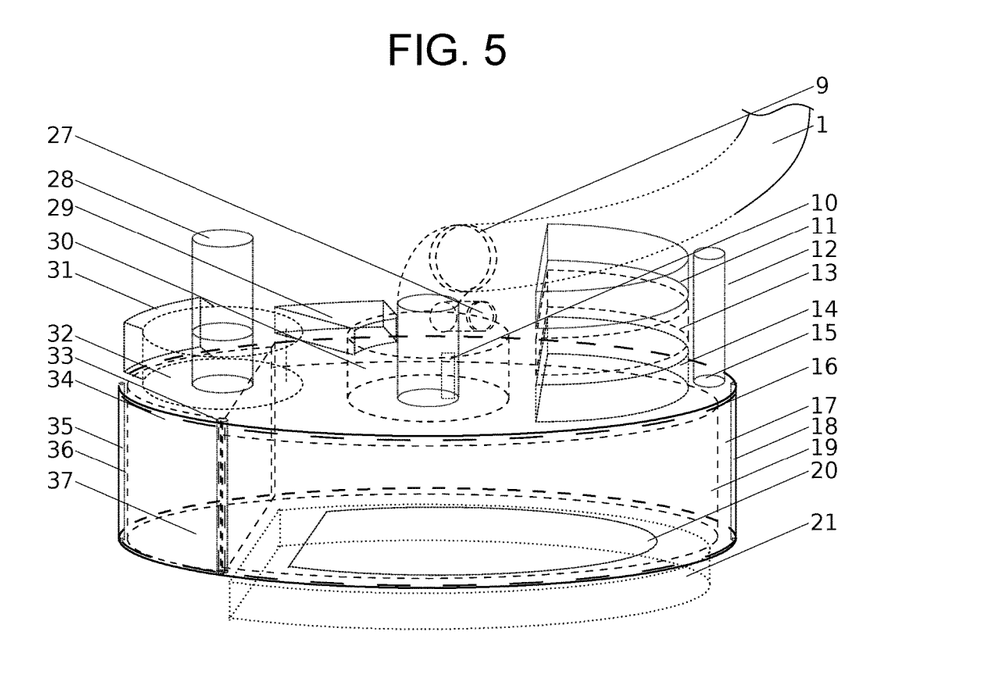
FIG. 5 is a view of the mask cleaning mechanism, with the water reservoir and heater and steam chamber.

FIG. 5 shows the water reservoir and waste water reservoirs and the chamber that holds the data logger, processor pumps and battery. The air hose filter connection 9 to the mask 45 comes off of the bi-direction air water pump 30. The pump has intakes for oxygen 27 (oxygen lines from oxygen source not shown). The bi-directional air water pump 30 is connected to a two way air intake valve with a pressure release that brings air into the bi-directional air water pump 30, and also releases air to the during the exhale cycle. Humidity and temperature are adjusted up by activating the ceramic heating unit 21 to release additional water vapor through the ceiling of the chamber of housing for removable water reservoir 17 and the floor chamber that holds the data logger, processor pumps and battery 12.

The chamber holds in water proof compartment (which is not specifically show in the drawing) holds the temperature sensor 10, the memory data logger module 11, the processor 13 and the battery 14 and the Wi-Fi/Bluetooth antenna.

The removable water reservoir 19 plays a key role as the water in it is heated by the ceramic heating unit 21 to create hot air and steam to go into the mask cleaning chamber, and it also provides adjustments for humidity and temperature. The heat is transferred to the removable water reservoir 19 through a metal heat conveyance module 20 that sits on the top of the ceramic heating unit 21 just below the removable water reservoir.

The waste water reservoir 39 in the waste water reservoir chamber 35 is filled through the waste water hose with drain 29 through activation of one-directional pump to clean air and water from the mask cleaning chamber 34.

Figure 6:
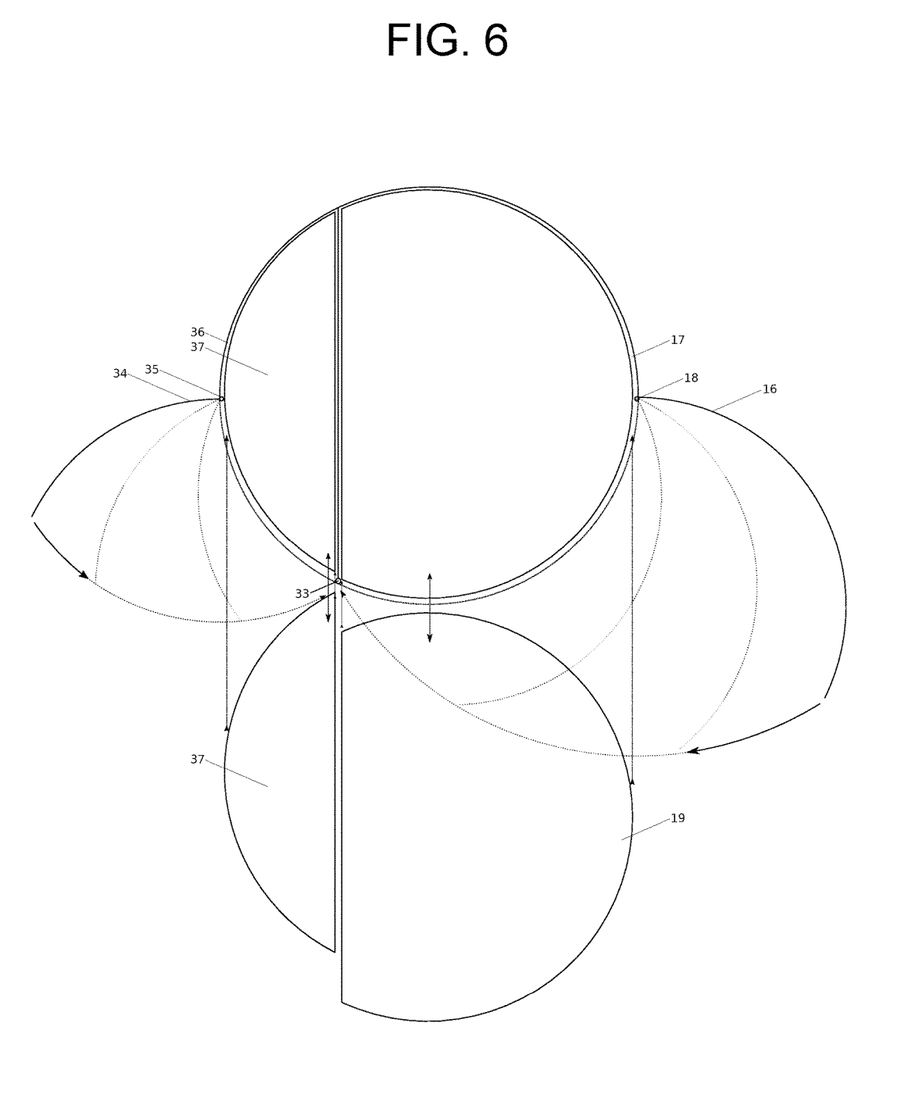
FIG. 6 is a view of the door that opens to remove the water reservoirs and door that opens to remove the waste water reservoir opening so the reservoirs can be removed.

FIG. 6 shows how the door for the removable waste water reservoir 37 is removed for the waste water chamber 36 and how the removable water reservoir 19 is removed for the chamber for the removable water reservoir chamber 17. For the removable waste water reservoir 37 the waste water reservoir door is opened 34 and the reservoir slides out the opening. For the removable water reservoir 19, the water reservoir door 16 is opened and the reservoir slides out the opening.

Figure 7:
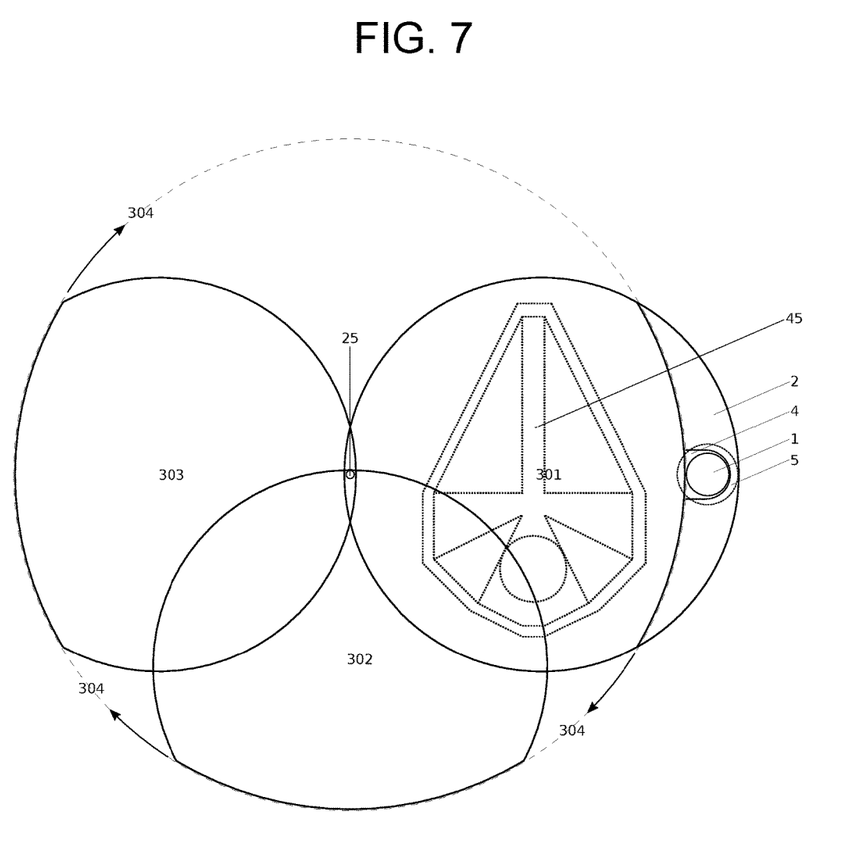
FIG. 7 shows how the mask cleaning chamber opens to accept the mask

FIG. 7 shows how the mask cleaning chamber opens to accept the mask. Movement is centered on the hinge for the cleaning chamber lid 25. Position 301 shows the mask 45 inside the lid, ready for cleaning. Position 302 shows the lid half open, and position 303 shows the mask in a full open position. The line 304 shows the path the mask cleaning chamber cover 3 leaning chamber covers while being opened or closed.

Figure 8:
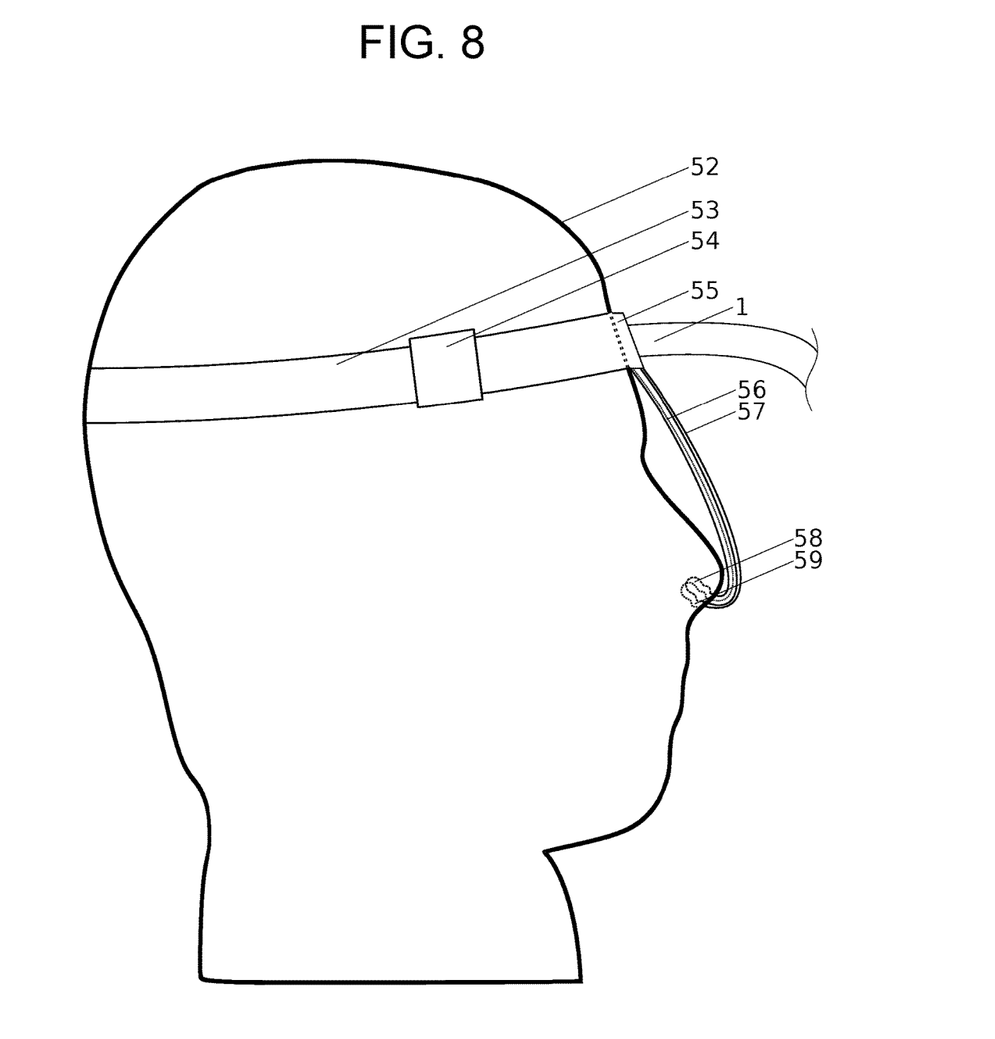
FIG. 8 details how the mask fits over the users face when in use.

FIG. 8 shows the mask 45 on a user's head detailing how the mask 45 fits on the head but also how air is delivered to the user. Parts of the mask in FIG. 2, including #s 39 through 44 are not shown on this Figure. Air flow goes to the user through a right flexible hose 56 to the right nasal bud 58, and a left flexible hose 57 to the left nasal bud 58.

Figure 9:
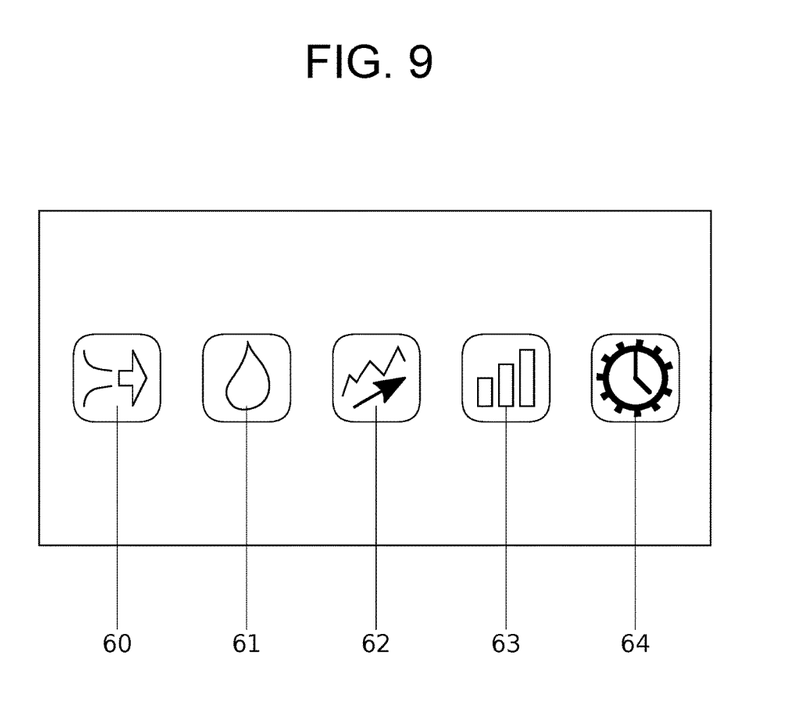
FIG. 9 is a view of the display with the second menu.

FIG. 9 show a view of the display 7 with the second menu icons as a sample of what the display will look like. Shown on the display are the Air flow icon 60. The Humidity icon, 61, the Monitoring level icon, 62, the Data logger icon, and the Use last settings icon, 64.

I claim:

1. A Continuous Bi-Level Positive Pressure (C/BiPAP) device for treating a patient suffering from sleep apnea comprising:
    a bi-directional air pump configured to push airflow to the patient and pull exhaled air from the patient through an air hose connected to a face mask;
    a control unit for controlling operation of the C/BiPAP device;
    a lithium battery for providing back-up power supply and for allowing the device to be transported and used outdoors;
    a housing comprising a top section forming a self-cleaning chamber for the mask and the bottom section comprising a chamber containing a ceramic heater;
    a cover on the self-cleaning chamber that opens and closes to selectively receive the mask for cleaning and storage;
    a water heater above the ceramic heater and configured to be heated by the ceramic heater when a self-cleaning process is initiated by the patient;
    vents in a top of the water reservoir and throughout the housing that all passage of warm air and steam from the water reservoir to the self cleaning chamber; and
    a vacuum pump for cleaning water and air in the self-cleaning chamber through a waste water hose with a drain to a waste water reservoir once the self-cleaning process is complete;
    wherein to perform the self-cleaning process on the mask the patient disconnects the air hose from the mask, inserts the mask into the self-cleaning chamber, inserts an end of the air hose holder on the mask cleaning cover, and initiates the self-cleaning process by pressing a button on the exterior of the housing.

2. The C/BiPAP device of claim 1, further comprising an oxygen sensor to determine the oxygen saturation level of the patient.

3. The C/BiPAP device of claim 2, further comprising an oxygen concentrator communicatively linked to the oxygen sensor.

4. The C/BiPAP device of claim 2, further comprising a carbon dioxide meter.

5. The C/BiPAP device of claim 1, further comprising an emergency condition system with audible alerts and alerts transferred wirelessly to a receiving station.

6. The C/BiPAP device of claim 1, further comprising at least one of a humidifier, heater/cooler, dehumidifier, filter, communication interface, a monitor and interface, and a medication chamber.

7. The C/BiPAP device of claim 1 further comprising at least one of a pulse meter, a blood pressure device, and a heart rate monitor.

8. The C/BiPAP device of 1, further comprising a communication device.

9. The C/BiPAP of claim 8, wherein the communication device transmits information between the patient and a medical professional or monitoring system.

* * * * *